(12) United States Patent
Venkatasetty

(10) Patent No.: US 7,232,511 B1
(45) Date of Patent: Jun. 19, 2007

(54) MULTI-GAS/VAPOR ELECTROCHEMICAL SENSOR FOR THE DETECTION AND MONITORING OF CHEMICAL AND BIOLOGICAL AGENTS

(75) Inventor: Hanumanthayana V. Venkatasetty, Burnsville, MN (US)

(73) Assignee: Panya, Inc., Burnsville, MN (US)

( * ) Notice: Subject to any disclaimer, the term of this patent is extended or adjusted under 35 U.S.C. 154(b) by 436 days.

(21) Appl. No.: 10/340,418

(22) Filed: Jan. 10, 2003

Related U.S. Application Data

(60) Provisional application No. 60/348,073, filed on Jan. 10, 2002, provisional application No. 60/371,562, filed on Apr. 10, 2002.

(51) Int. Cl.
  *G01N 27/327* (2006.01)
(52) U.S. Cl. .............................. 204/403.01; 204/403.06
(58) Field of Classification Search ..............................
  204/403.01–403.15, 416–418, 421–426, 204/411–412
  See application file for complete search history.

(56) References Cited

U.S. PATENT DOCUMENTS

| | | | | |
|---|---|---|---|---|
| 4,336,121 A * | 6/1982 | Enzer et al. | ........... | 204/403.02 |
| 4,472,353 A * | 9/1984 | Moore | ......................... | 422/58 |
| 4,785,658 A * | 11/1988 | Jackson | ..................... | 73/31.01 |
| 5,120,421 A * | 6/1992 | Glass et al. | .................. | 204/406 |
| 5,322,611 A * | 6/1994 | Zaromb | ...................... | 204/424 |
| 5,466,575 A * | 11/1995 | Cozzette et al. | ............... | 435/6 |
| 5,527,446 A * | 6/1996 | Kosek et al. | ............ | 205/792.5 |
| 5,716,506 A * | 2/1998 | Maclay et al. | .............. | 204/424 |
| 5,832,411 A * | 11/1998 | Schatzmann et al. | ......... | 702/23 |
| 5,841,021 A * | 11/1998 | De Castro et al. | ........... | 73/23.2 |
| 6,171,238 B1 * | 1/2001 | Klimes et al. | .............. | 600/345 |
| 6,606,897 B1 * | 8/2003 | Koyano et al. | .............. | 73/23.2 |
| 6,623,698 B2 * | 9/2003 | Kuo | .......................... | 422/68.1 |

FOREIGN PATENT DOCUMENTS

| | | | |
|---|---|---|---|
| DE | 29601472 U1 | * | 5/1996 |
| GB | 1322330 | * | 7/1973 |
| JP | 63-222256 A | * | 9/1988 |

(Continued)

OTHER PUBLICATIONS

JPO computer translation of Takashi et al. (JP 05-273175 A), Oct. 22, 1993.*

(Continued)

*Primary Examiner*—Alex Noguerola
(74) *Attorney, Agent, or Firm*—Garlick Harrison & Markison; James A. Harrison

(57) ABSTRACT

A silicon substrate device is formed to include circuitry for testing for various agents of interest. The novel solid state miniaturized microprocessor based electro-chemical sensor device includes a substrate with a plurality of electrodes formed thereon for sensing the various agents of interest. A cell structure includes electrodes deposited over silicon dioxide over a silicon substrate. Circuitry is formed within a semiconductor portion formed within a portion of the silicon substrate or, alternatively, formed in a separate solid state device or substrate material (doped substrate to generate biasing voltages to the electrodes in the silicon substrate to detect the agent of interest. A polymer film or membrane is formed upon the electrodes to receive and pass the agent of interest to allow detection by the electrodes.

25 Claims, 12 Drawing Sheets

FOREIGN PATENT DOCUMENTS

JP 05-273175 A * 10/1993
JP 08-201336 A * 8/1996

OTHER PUBLICATIONS

JPO computer translation of Takashi et al. (JP 08-201336 A), Aug. 9, 1996.*

Derwent abstract of WOM GMBH Innovative Prod. Medizin & Tech (DE 29601472 U1), May 23, 1996.*

JPO abstract of Ikariyama et al. (JP 63222256 A), Sep. 16, 1988.*

CAPLUS abstract of Giner et al. ("Preparation and characterization of platinum black for anodic hydrocarbon oxidation," Preprints of Papers—American Chemical Society, Davison of Fuel Chemistry (1967), 11(3), 123-33), publication month unknown.*

Fasman et al. "Modification of platinum black with chlorides of alkaline earth metals," Zhurnal Fizicheskoi Khimii (1972), 4698), 2015-9), publication month unknown.*

CAPLUS abstract of Kinoshita et al. ("Characterization of platinum electrocatalyst. Examination of platinum crystallite size, morphology, and porosity of supported and unsupported platinum blacks," Fine Part., Int. Conf., Pap. 2nd (1974), Meeting Date 197, publication month unknown.*

CAPLUS abstract of Kinoshita et al. ("Changes in the morphology of platinum agglomerates during sintering," Electrochimica Acta (1973), 18(12), 953-61), publication month unknown.*

CAPLUS abstract of Imamura et al. (JP 2001141696 A2), May 25, 2001.*

CAPLUS abstract of Imamura et al. (JP 2001066289 A2), Mar. 16, 2001.*

CAPLUS abstract of Villeneuve et al. ("Electrochemical detection of nitric oxide production in perfused pig coronary artery : comparison of the performances of two electrochemical sensors," Journal of Pharmacological and toxicological Methods (1998), 4092), publication month unknown.*

CAPLUS abstract of Pyke (WO 9636869 A1), Nov. 21, 1996.*

Niiro et al. ("Changes in nitric oxide generation in rats with global ischemia: in vivo measurements using a nitric acid sensor," Neurosciences (Okayama, Japan) (1995), 21(3), 143-50), publication month unknown.*

Table 6.1 of Corrosion—vol. 1—Metal/Environment Reaciotns, ed. Shrier et al., Butterworth Heinemann, 2000.*

* cited by examiner

FIG. 1 preliminary sensor design

FIG. 4 high sampling rate cell using turbulent mixing

FIG. 8 detection range of proposed dosimeter and all clear detector compared to some existing chemical agent detection systems FIG. 10 plug-in dosimeter FIG. 11 dosimeter and all clear alarm

MULTI-GAS/VAPOR ELECTROCHEMICAL SENSOR FOR THE DETECTION AND MONITORING OF CHEMICAL AND BIOLOGICAL AGENTS

CROSS REFERENCE TO RELATED APPLICATIONS

This application incorporates by reference, is related to, claims the benefits of the following Provisional Applications for Patent having Ser. No. 60/348,073 filed on Jan. 10, 2002 and 60/371,562 filed on Apr. 10, 2002 under 35 U.S.C. 119(e).

BACKGROUND

1. Technical Field

The present invention relates to systems and methods for detecting the presence of chemical and biological agents and, more particularly, to solid state devices for detecting the presence of chemical and biological agents.

2. Related Art

The need for systems for testing against biological and chemical agents has become painfully clear recently. Current systems for testing for such agents, as well as for testing for polluting agents, have the drawbacks of not being truly portable, or, alternatively, of requiring test procedures in which results are only obtained after a period of time has elapsed. FIG. 1 illustrates an electrochemical gas sensor for use as an electrochemical sensor. As may be seen, a body of the sensor includes a rubber gasket, a micro porous Teflon plate and a lid. The body is formed to contain electrolyte that reacts with a sensor to detect a specified agent. One problem with the sensor design of FIG. 1, however, is that it does not provide the agent detection as reliably and portably as is desirable.

It would be very advantageous, therefore, to have a system and method for testing for agents of interest in a real time manner that comprises truly portable equipment as well as stationary equipment for placement at specified checkpoints.

SUMMARY OF THE INVENTION

A silicon substrate device is formed to include circuitry for testing for various agents of interest. The novel solid state miniaturized microprocessor based electro-chemical sensor device includes a substrate with a plurality of electrodes formed thereon for sensing the various agents of interest. In one embodiment of the invention, a cell structure that includes the electrodes is deposited over silicon dioxide over a silicon substrate (undoped or a at least an undoped portion). Circuitry is formed within a semiconductor portion formed within a portion of the silicon substrate or, alternatively, formed in a separate solid state device or substrate material (doped substrate). The circuitry is formed to generate biasing voltages to the electrodes in the silicon substrate to facilitate detection of an agent of interest. A polymer film or membrane is formed upon the electrodes to receive and pass the agent of interest to allow detection by the electrodes.

As the detection of different agents sometimes requires different biasing voltages, one embodiment of the present invention includes a plurality of sensing cells, each of which includes a plurality of electrodes formed underneath a polymer film or membrane and biasing circuitry to bias the electrodes to prompt detection of the agents of interest.

The inventive device further includes circuitry for determining that an agent of interest has been detected and for determining the type of detected agent of interest. Further, the circuitry is formed to produce an indication that an agent has been detected and for identifying the agent or a list of suspected agents based upon the cell that detected the presence of an agent and the concentration of the agent.

The invention may be implemented in many different embodiments. For example, it may be formed within disposable buttons, hand-held devices or even stationary devices. Moreover, the invention may be formed to include circuitry for communicating with an external device coupled to a network. The network may be either a wireless network or a wireline network. One embodiment of the invention includes logic circuitry to generate a plurality of alarms according to the certainty of the identity of a detected agent and according to the class or category of the detected agent. The alarms may be generated for transmittal to an external device or for detection by an individual either through aural or visual mediums.

DETAILED DESCRIPTION

FIG. 2 is a cross section of a solid state electromechanical sensor formed according to one embodiment of the present invention. As may be seen, the sensor is fabricated on a silicon wafer using know techniques for fabricating semiconductor devices. The agent generally includes a silicon substrate upon which a layer 12 of silicon dioxide is formed. Plurality of contact pads are formed thereon as well as counter electrodes, sensing electrodes, reference electrodes, a polymer firm formed on the electrodes and a Teflon membrane formed at least partially over the polymer film.

A fast response time sensor for detecting undesirable materials or agents includes a unique non-aqueous electrolyte solution consisting of binary and/or ternary non-aqueous solvent mixtures with high boiling point (~240° C.) and low freezing point (~−40° C.) and high electrolytic conductivity and electrochemical stability. The electrolyte solution (1M) contains tetrabutylammonium hexaflurophosphate, an electrochemically stable salt. The solution is non-toxic and non-corrosive with a wide voltage window (0 to −3 V and 0 to +2.5 V) with inert noble metal electrodes. The electrolyte solution is formed within the polymer film.

The membrane electrolyte film compositions have been improved to make them very hydrophobic so that moisture from the environment can not enter into the film composition and interfere with the detection and measurement of the toxic chemicals, their vapors and other toxic gases of interest to the project. They have been improved to make them suitable for the detection and monitoring of Bio-warfare Agents. The specific composition of the electrolyte film depends upon, in one embodiment of the invention, the agents that are to be detected. For example, if the agents are chemical war agents, the membrane electrolyte film is very thin (100 to 150 micrometers) and its composition is made of nontoxic and non-corrosive solvent mixture of propylene carbonate, ethylene carbonate and dimethyl carbonate in the ratio of 45:40:15 and 50:40:10 vol % respectively containing a stable salt, tetrabutylammonium hexafluorophosphate at one molar concentration.

This electrolyte solution with the highest conductivity (8 to $10X^{-3}$ S/cm) at 25° C. is immobilized in a polymer matrix of poly(methylmethacrylate) (PMMA) (24 to 30 wt %) and poly (vinylidene fluoride) (PVDF) (2 to 5 wt %) by warming the solution to about 80° C. with stirring to make a viscous liquid. We add known amounts (0.2 to 3 wt %) of specially treated fumed silica (5 to 20 nm) particles (silazanes) with hydrophobic trimethylsilyl surface groups. This additive helps to enhance the hydrophobic property of the membrane and increase the size of the free volume elements in the membrane film facilitating the diffusion of organic chemical agent molecules. These materials are electrochemically stable and chemically compatible with the electrolyte.

If the agents to be detected are biowarfare agents, the membrane electrolyte film is made selective to biowarfare agents like Anthrax, Smallpox, Botulism by incorporating into the membrane film certain inorganic coordination compounds such as Platinum(11) acetylacetonate and Platinum (11) 2,4 pentanedionate. These Platinum ions of the coordination compounds have the affinity or the ability to complex with the biowarfare agents by entrapping oligonucleotides and lead to the detection of target DNA of the warfare agents at the electrode where they can be detected by voltammetric techniques. This process is improved by adding to the membrane composition nanosize particles of materials such as Titanium dioxide (1 to 3 micrometer) which will increase the porosity in the membrane.

The electrode structure of the solid-state sensor cell is formed of common electrode construction for some embodiments of the invention according to the application. For other applications, the embodiment, and more particularly, the electrode, can be modified for potential application in the detection of bio-warfare agents. Sub-micron sized platinum electrodes will be used in the miniaturized cell and are coated electrochemically with a thin layer of platinized-platinum (platinum-black) using a solution of chloroplatinic acid.

The resulting platinized electrodes become porous (large surface area) and they become highly catalytic. The plating conditions such as the current density, plating bath temperature and plating time will be varied so that the particle size of plated platinized-platinum are also of sub-micron size as determined by the Scanning Electron Microscopy (SEM) and other advanced surface characterization techniques.

The sub-micron size particles being porous with pore sizes in the range of 50 to 200 Angstroms have the potential to directly bind and immobilize the antigen of the bio-warfare agent molecule and can retain their activity. The bound complex is amenable to direct electrochemical oxidation and on applying the specific voltage in presence of a small amount of hydroquinone compound. This process will give rise to characteristic current-voltage curves. The applied voltage is characteristic of the bio-warfare agent and the current amplitude is proportional to the concentration of the toxin.

Similarly, sub-micron sized electrodes of metals like iridium, ruthenium and rhodium can be used and the oxides of these metals, particularly, iridium electrochemically generated are highly porous with three dimensional structure and are potentially attractive for binding antigens of bio-warfare agents. Alternatively, the platinized-platinum electrodes and other metal electrodes can be coated with a suitable antibody material. The modified electrode surfaces will be able to bind and immobilize bio-warfare agents forming an antibody-antigen complex. This complex will result in changes in the properties of the bio-warfare agent and the electron transfer reactions between the complex and the electrode can take place easily in presence of suitable reagents.

By applying a suitable voltage to the sensing electrode, electrochemical reactions can take place thereby giving rise to current-voltage curves where the voltage is characteristic of the bio-warfare agent and the current amplitude is proportional to the concentration of the toxin. The formation of the antibody-antigen complex will also give rise to changes in the capacitance of the sensor cell which can also be used as a measure of the nature of the agent for identification purpose and possibly concentration.

The sensor cell for the bio-warfare agent detection can be made with more common electrode materials in place of the platinum. Sub-micron sized electrode materials can be of gold and carbon. Alloys of metals such as platinum-iridium, platinum-rhodium to mention a few can be used. Sub-micron sized electrodes of the electrochemical cells have the potential to bind directly with the antigen of the bio-warfare agent and can undergo electrochemical reaction. Electrochemical cells with two electrodes instead of three electrodes can be used for the detection of single bio-warfare or chemical agent or any potentially toxic chemical species.

The unique properties of the non-aqueous electrolyte is summarized in Table 1. The electrolyte has very low vapor pressure of 0.03 mm of Hg compared to aqueous electrolyte with about 20 mm of Hg at 20° C. It has very high solubility for gases, vapors and organic chemicals by more than an order of magnitude compared to aqueous electrolyte solution.

Figure 1:
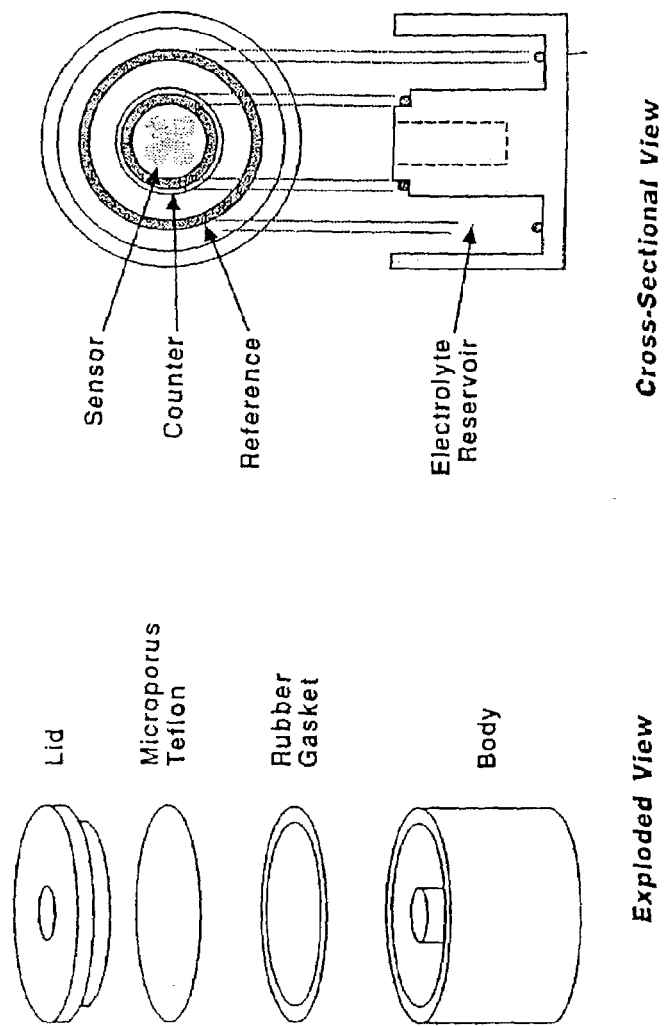
FIG. 1 illustrates an electrochemical gas sensor for use as an electrochemical sensor.
Figure 2:
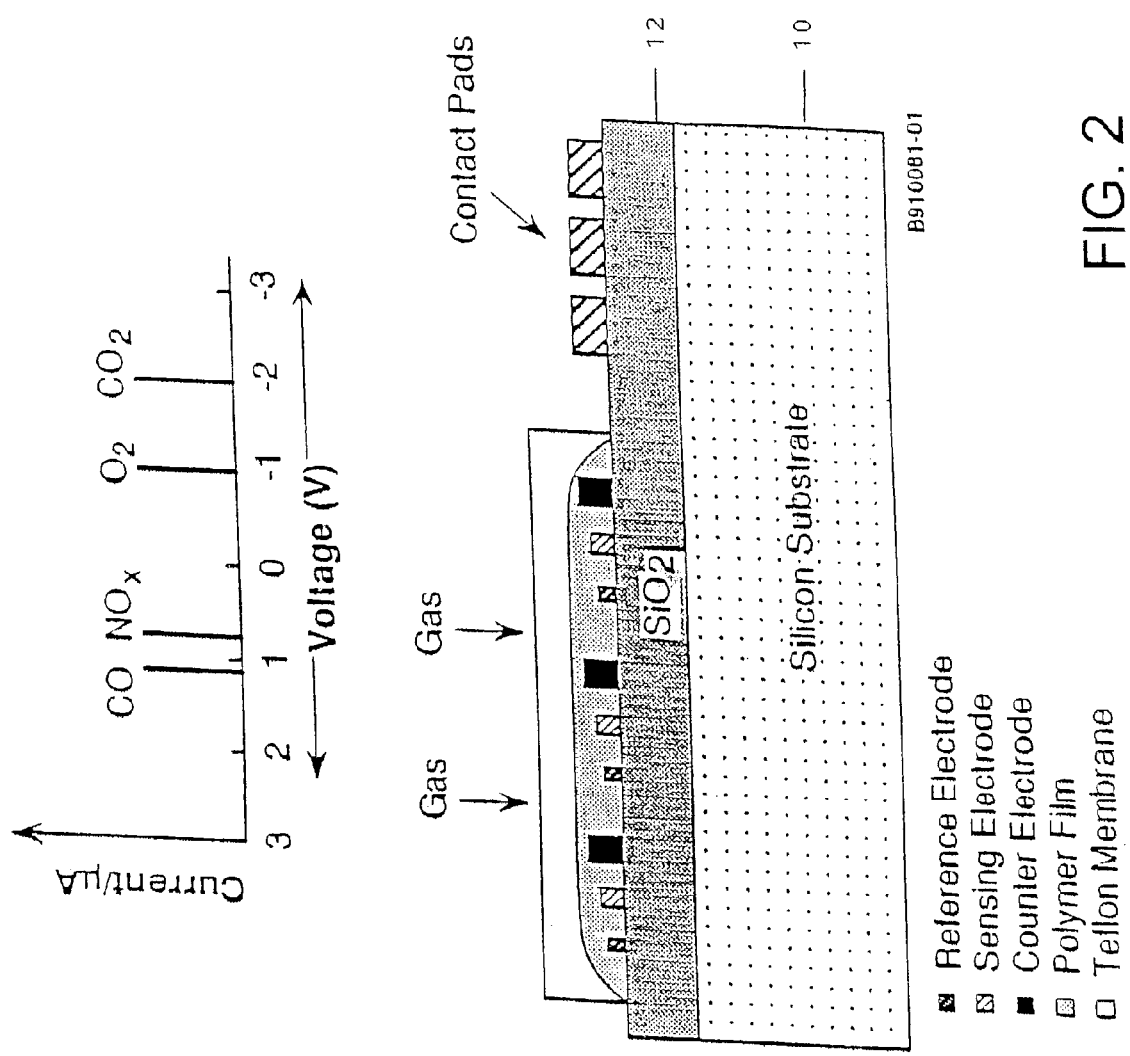
FIG. 2 is a cross section of a solid state electromechanical sensor formed according to one embodiment of the present invention.

A miniaturized electrochemical cell has an inter-digitated three-electrode structure of platinum sensing, platinum counter and platinum reference electrode deposited on a substrate of silicon dioxide over silicon wafer shown in FIG. 2b of the appended document entitled "Eletrochemical Gas Sensors". The cell is coated with a thin membrane containing the electrolyte solution immobilized by a polymer matrix material of poly (methyl methacrylate) and poly (vinylidene fluoride) or poly (acrylonitrile) or their mixtures.

Figure 3:
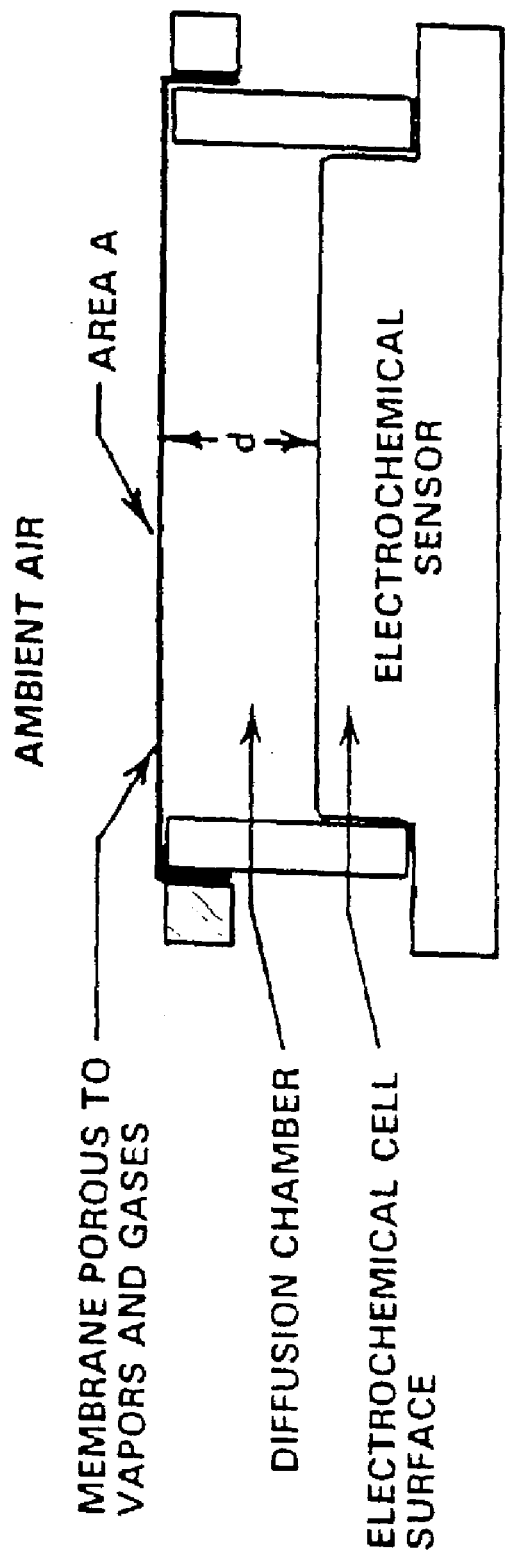
FIG. 3 is a sensor formed according to one embodiment of the invention.

The electrochemical cell, as shown in FIG. 3, illustrates one embodiment of the sensor, containing the membrane electrolyte with a wide voltage window that can oxidize or reduce the toxic gases, vapors or toxic organic-based chemical and/or biological agents giving rise to diffusion current whose amplitude is proportional to the concentration of the chemical species that are under going redox process as shown by the relationship:

$$I_1 = \frac{nFA}{d} C$$

where $I_1$ is the diffusion current, "n" is the number of electrons transferred, "F" is the Faraday constant, "A" is the electrode surface area, "d" is the diffusion layer thickness and, "C" is the concentration of the chemical species. The diffusion chamber shown in FIG. 3 may be utilized with the solid state electromechanical sensor of FIG. 2 as is illustrated herein FIG. 3.

The three-electrode structure of the cell provides good control on voltage applied to the sensing electrode and thus improving the selectivity of the sensor. This combined with wide voltage range and using cyclic voltage signals (e.g., a square wave) makes the sensor ideal for multi-gas or multi-vapor or chemical sensor so that more than one chemical can be detected almost simultaneously with one sensor. It can be used as a dosimeter or a monitor.

The sensor includes logic for self-calibration and self cleaning. The logic periodically monitors the impedance of the sensing electrode and cleans the sensing electrode surface due to electrode fouling by applying an elevated voltage to the electrode for short duration to burn off any deposition of material. The logic tunes the oxygen reduction voltage to −1 volt and calibrates using oxygen of ambient air periodically. The logic may be in the form of solid state logic or may be formed using preprogrammed microprocessor controlled electronics.

The membrane used in the present invention is one that passes the agents of interest to allow detection by the electrodes. The non-aqueous electrolyte-based membrane has the following composition in one embodiment of the invention: Solvent mixture consists of Propylene carbonate (PC), Ethylene carbonate (EC) and Dimethyl carbonate (DMC). These solvents are nontoxic and non-corrosive. The solvent mixture has PC composition varying from 40 to 60% by volume, the optimum is 45%; EC composition varying from 30 to 45% by volume, the optimum is 40%; and DMC composition varying from 10 to 20% by vol, the optimum is 15%. The solute is tetrabutylammoniumhexa-fluorophosphate at 1.0 Molar.

The conductivity of the electrolyte varies from $8 \times 10^{-3}$ to $10 \times 10^{-3}$ Siemens/cm at room temperature with $8.5 \times 10^{-3}$ Siemens/cm being optimum. The electrolyte has very high boiling point (~200 degrees centigrade) and low freezing point (~−40 degrees centigrade). The polymer matrix materials have two components, namely: Polymethylmethacrylate (PMMA) which is a major part of the membrane that helps to retain the electrolyte material and its composition varies from 24 to 30% by weight, the optimum being 24% and the second component, Polyviniledene fluoride (PVDF) its function is to provide mechanical integrity for the membrane film and being a fluorinated material, it is hydrophobic, i.e., has water or moisture repellent property and makes the membrane film almost free from moisture. Its composition varies from 2 to 8% by weight, the optimum being 6%. In addition, we place a thin micro-porous membrane of Teflon with 0.45 micrometer size pores with polypropylene backing on the membrane to further prevent any moisture entering into the sensor cell.

Figure 4:
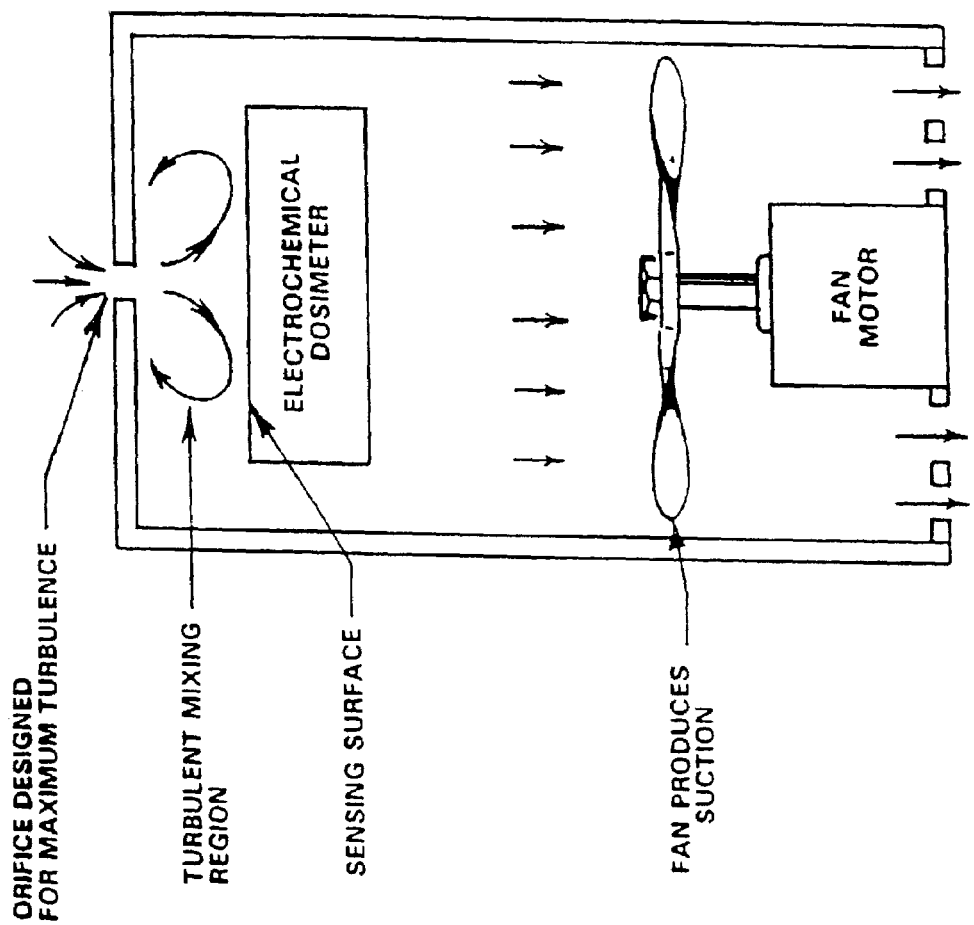
FIG. 4 illustrates another embodiment of the present invention.
Figure 5:
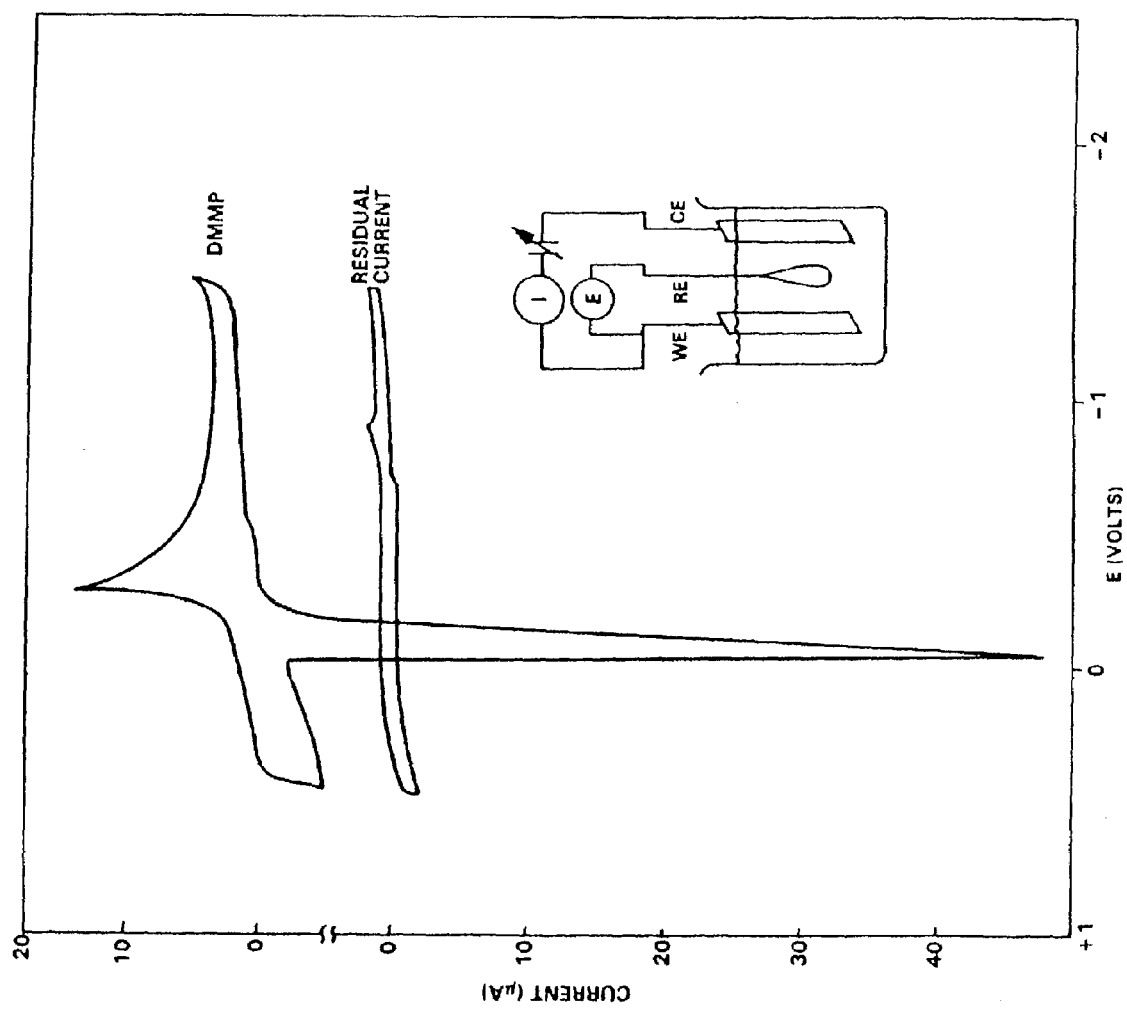
FIGS. 5–9 illustrate test results for different embodiments of the present invention.
Figure 6:
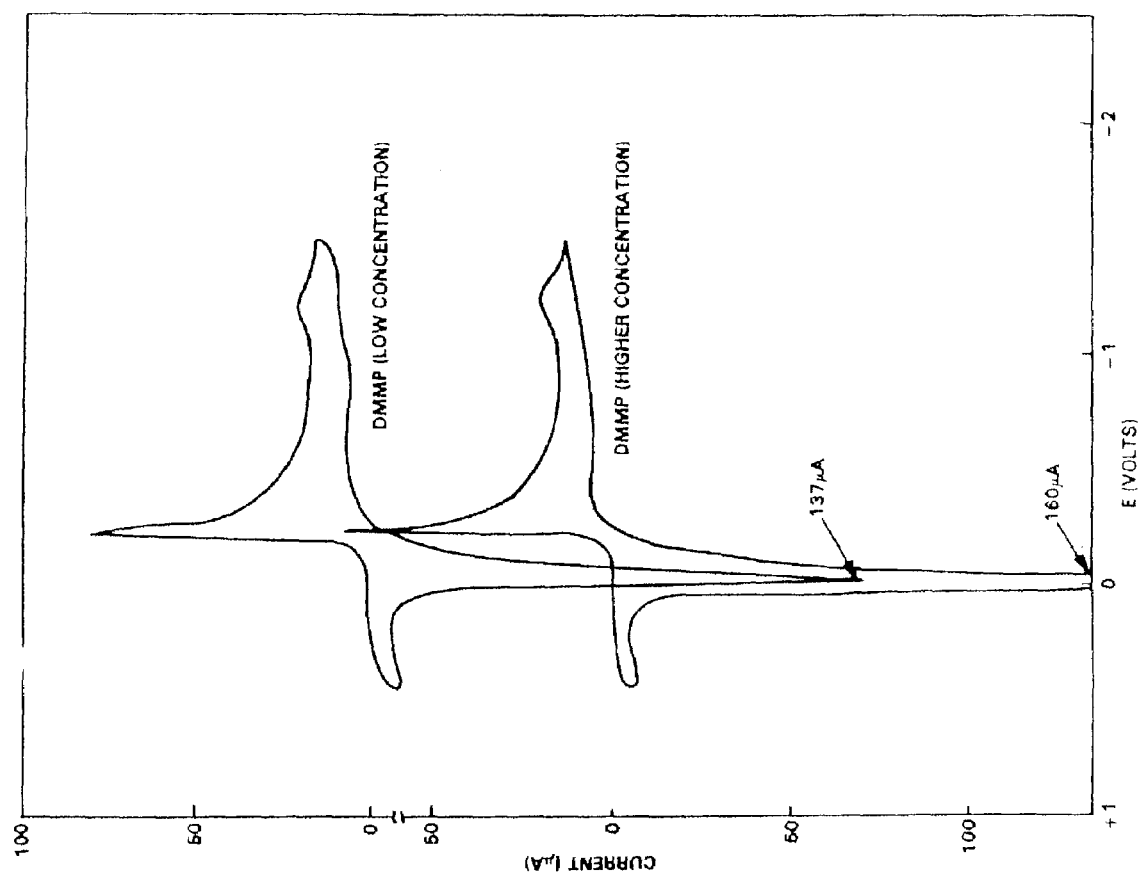
Figure 7:
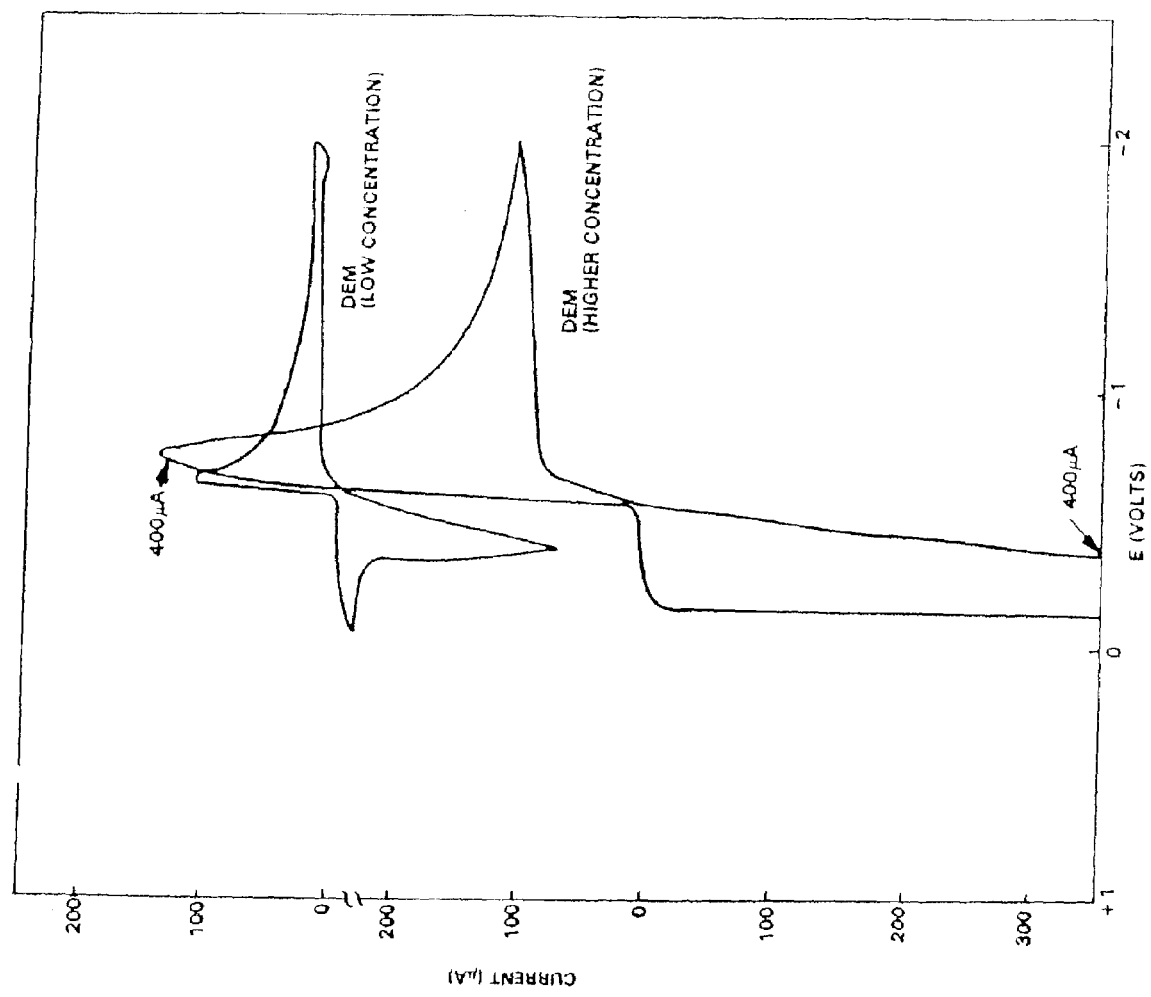
Figure 8:
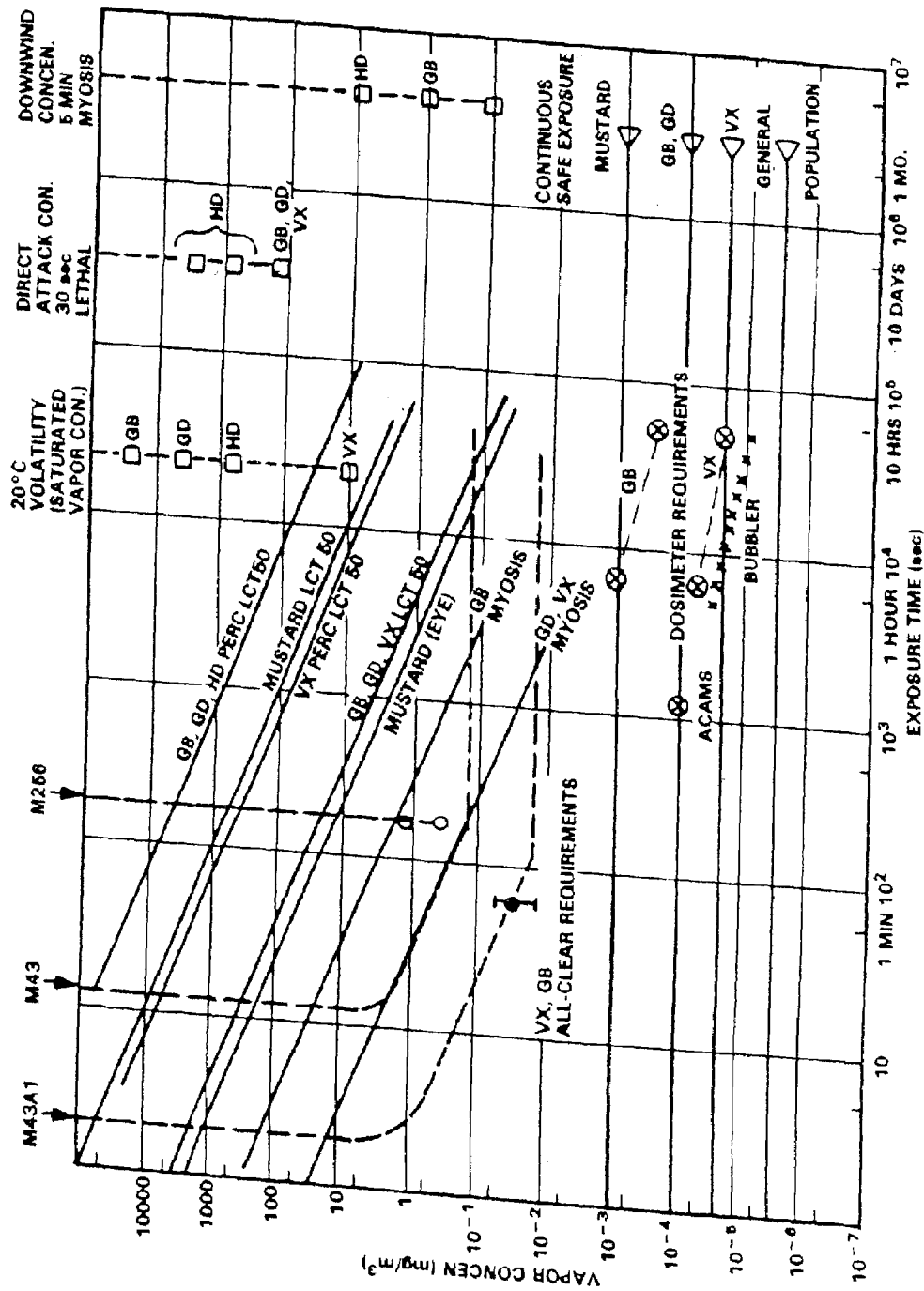
Figure 9:
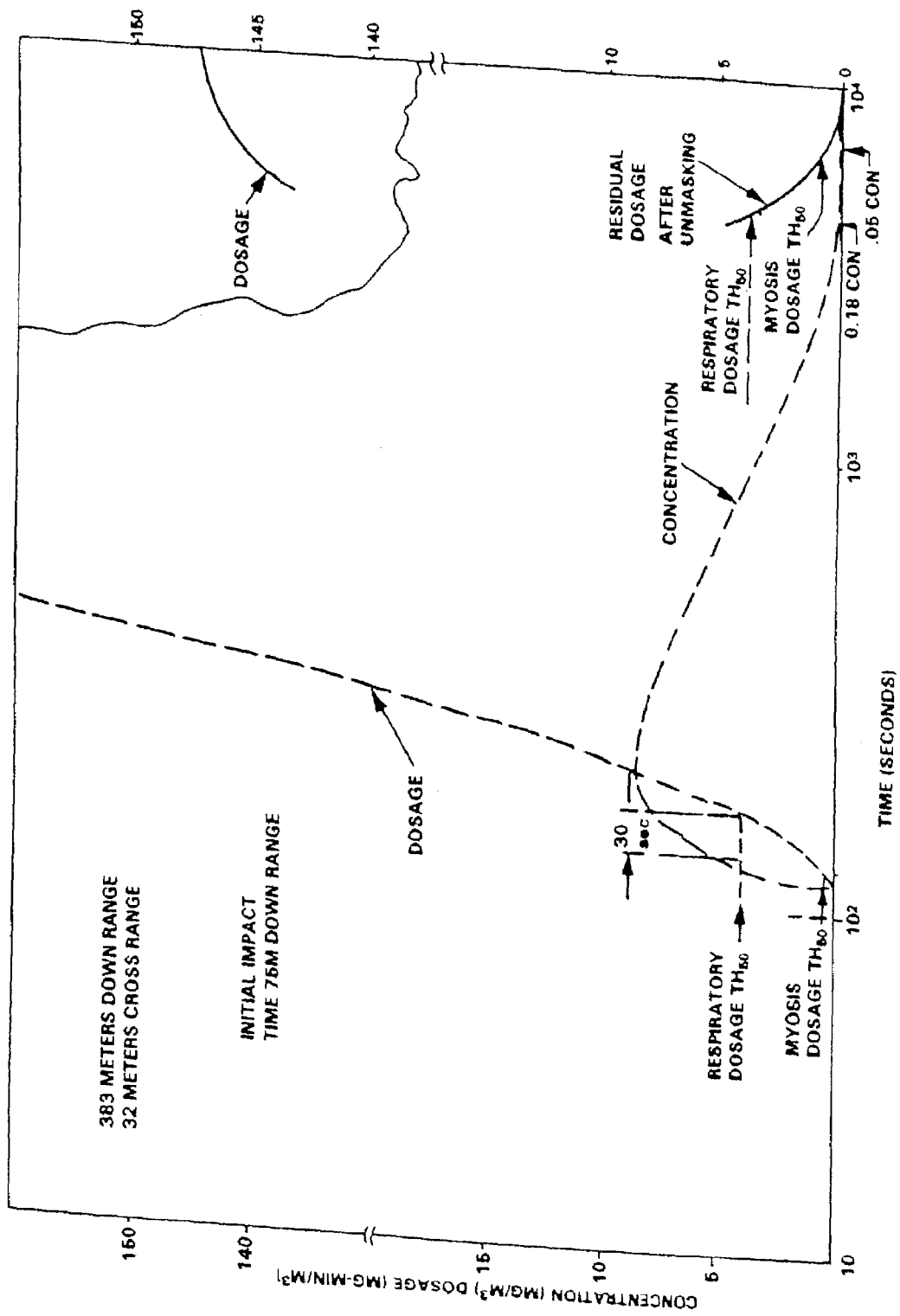

FIG. 4 illustrates another embodiment of the present invention in which a system for turbulent mixing enhances the ability for the sensor to detect the agent(s) of interest. Such an embodiment may readily be implemented in a hand held unit.

The high solubility of chemical species in the electrolyte improves the detection sensitivity. To improve the sensitivity further, the "Diffusion Cell" for gas sampling, as well as a "High Sampling Rate Cell" using Turbulent Mixing may be used as shown in FIGS. 3 and 4. The high boiling points of the solvent mixture of propylene carbonate, ethylmethyl carbonate and gamma-butyrolactone and the addition of gelling agents results in very low vapor pressure of the electrolyte solution and thus increases the operating life (2 years) and the shelf life of the sensor (5 years). FIGS. 5–9 illustrate test results for different embodiments of the present invention. The test results generally illustrate voltage/current curves for a sample compound of dimethymethyl phosphonate (DMMP) with a concentration of 2 to 10 parts per million (PPM) in nitrogen. Other test result are shown for diethyl melonate (DEM) with similar concentration levels allowed in a test chamber. Generally, the test results illustrate typical sensitivities (agent identification) for the various embodiments of the invention. Similar results have been achieved with prior art testers that utilize liquid electrolytes (rather than solid state electronics).

Figure 10:
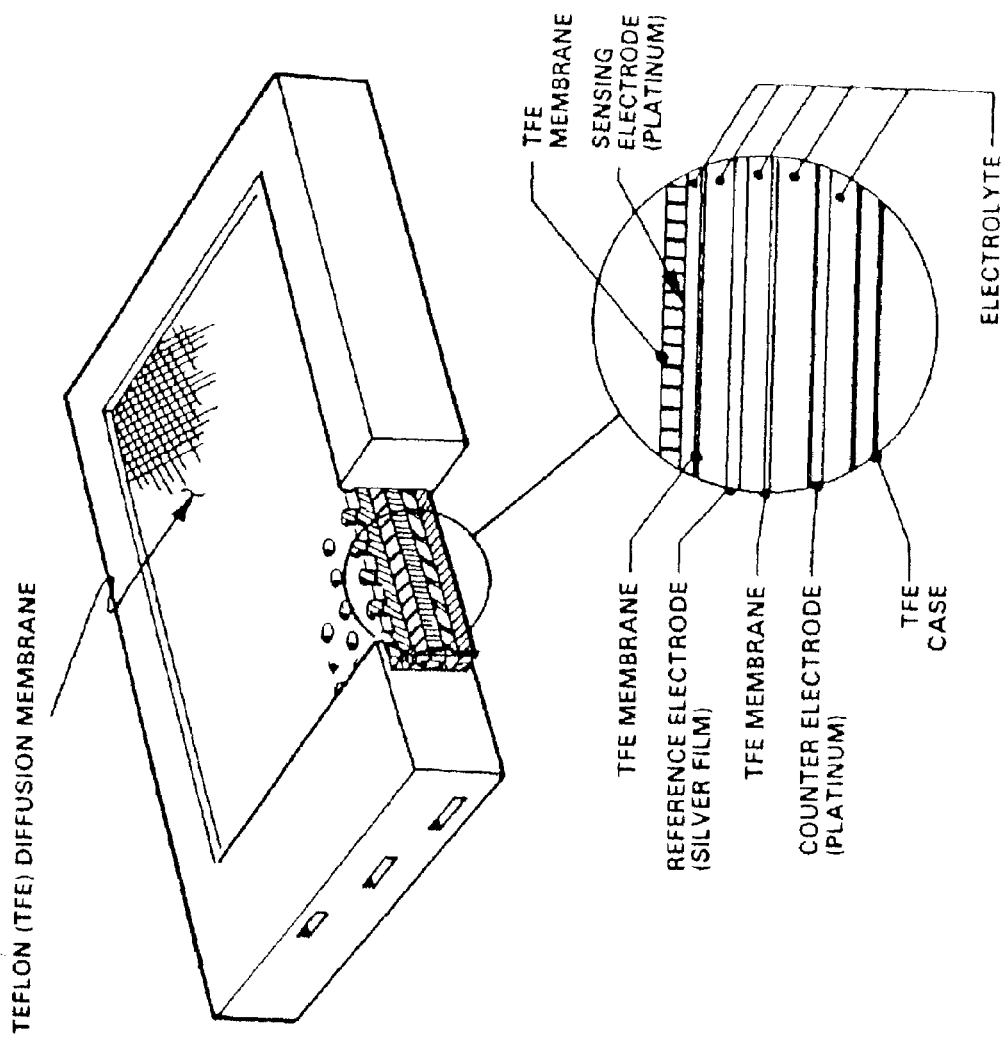
FIGS. 10 and 11 illustrate one embodiment of the invention.
Figure 11:
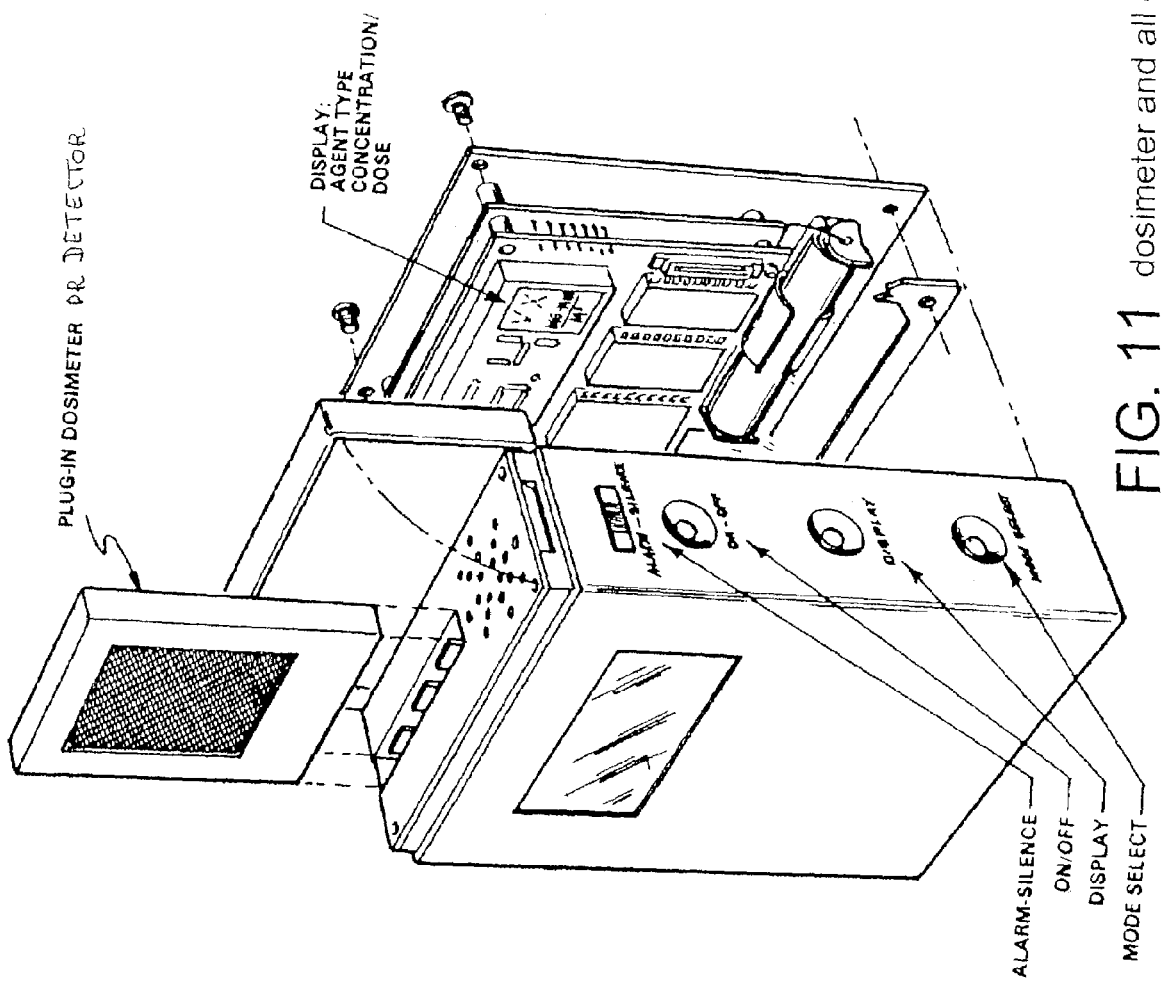

FIGS. 10 and 11 illustrate one embodiment of the invention in which a plug in cartridge is formed with the inventive concepts for inserting into a larger data processing system.

Figure 12:
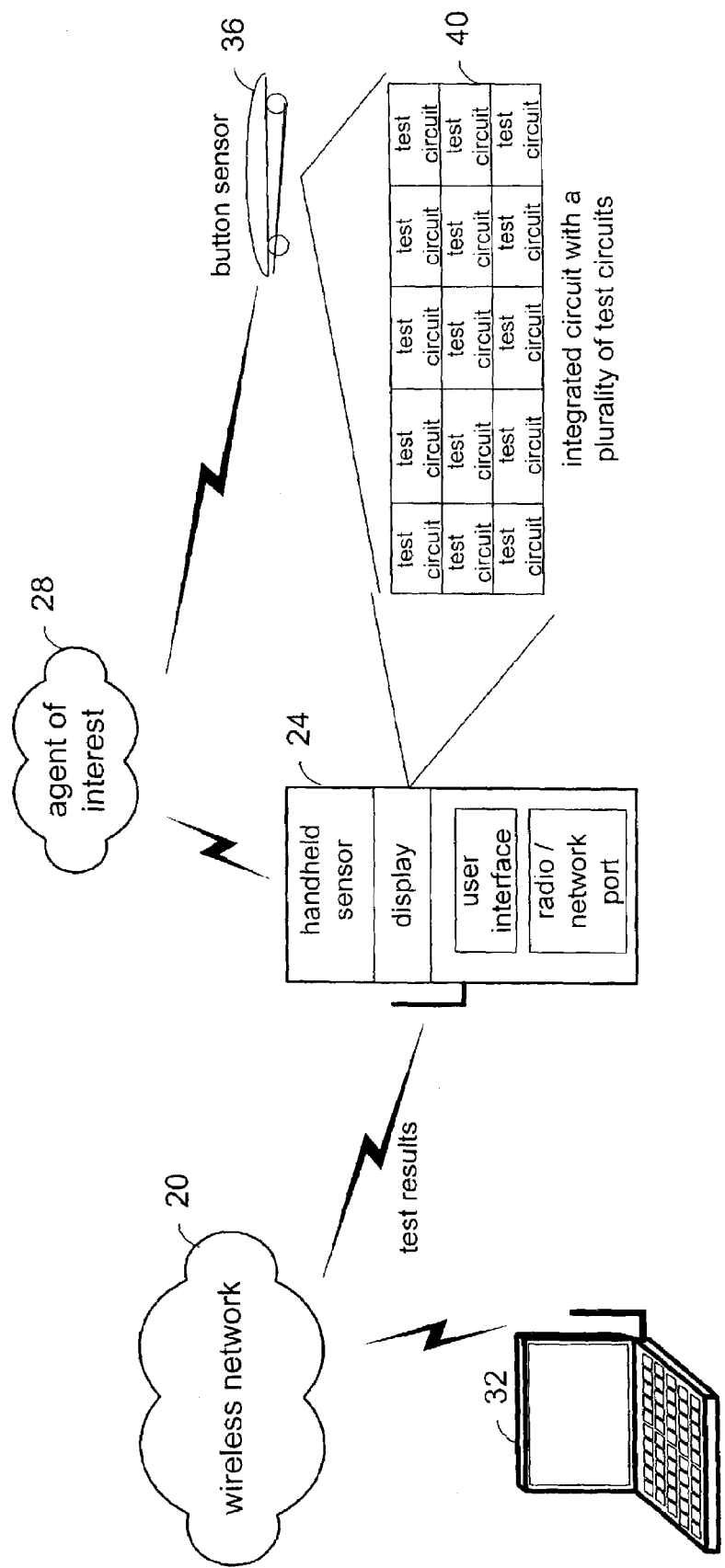
FIG. 12 is a functional block diagram that illustrates multiple embodiments of the present invention.

FIG. 12 is a functional block diagram that illustrates multiple embodiments of the present invention. Referring to FIG. 12, a wireless network 20 communicates with a handheld sensor 24 by way of a wireless communication link. Handheld sensor 24 detects agents of interest in the environment such as agent of interest 28. Handheld sensor 24 performs its tests to detect agent of interest 28 and produces the test results an external device by way of wireless network 20. In the example shown, handheld sensor 24 produces the test results to a wireless terminal 32 that also communicates through wireless network 20. It is understood, however that wireline networks and couplings may be substituted for the wireless network shown in FIG. 12. As may also be seen examining FIG. 12, the handheld sensor includes a radio/network port for communicating with one of a wireless or wireline network.

A button sensor 36 also is shown in FIG. 12. Button sensor 36 includes circuitry for detecting agent of interest 28. In the described embodiment, button sensor 36 includes at least one light emitting diode (LED) that illuminates to indicate detection of an agent of interest. In an alternate embodiment, button sensor 36 includes a plurality of light emitting diodes wherein the diodes are powered to define a binary or other code to identify the agent of interest. In this particular embodiment, four light emitting diodes are utilized to identify any one of 16 different agents or groups of agents of interest. It is understood, of course, that different numbers of diodes or user interfaces may be implemented on a button sensor to convey information to the user.

Any sensor formed according to the present invention may be formed to define logic for testing only one or a plurality of agents of interest. In the example of FIG. 12, both the handheld sensor and the button sensor include an integrated circuit 40 that includes a plurality of test circuits wherein each test circuit is formed to provide test logic for a specified agent or groups of agents of interest. In the described embodiment, the integrated circuit includes fifteen test circuits. As may also be seen, handheld device 24 further includes a display and a user interface to communicate with the user to enable the user to specify test parameters and to view options and test results.

While the invention is susceptible to various modifications and alternative forms, specific embodiments thereof have been shown by way of example in the application herein. It should be understood, however, that the specific embodiments illustrated herein are not intended to limit the invention to the particular forms disclosed. On the contrary, the invention is intended to cover all modifications, equivalents and alternatives falling within the spirit and scope of the present invention.

The invention claimed is:

1. A solid state agent sensor, comprising:
a plurality of sub-micron sized inert noble metal electrodes formed on a silicon wafer, the electrodes for detecting at least one agent of interest;
circuitry coupled to the plurality of electrodes for generating a biasing voltage for producing the biasing voltage to at least one electrode of the plurality of electrodes; and
a membrane comprising an electrolyte solution formed within a polymer film to cover the plurality of electrodes for passing the at least one agent of interest to at least a portion of the plurality of electrodes wherein the solid state agent sensor is operable to generate at least one voltage to detect at least one agent of interest, wherein, the electrolyte solution of the membrane covering the plurality of electrodes comprises non-aqueous electrolytes, a stable salt, a polymer matrix materials, fumed silica particles and hydrophobic trimethylsilyl surface groups.

2. The solid state agent sensor of claim 1 wherein the electrolyte comprises a solvent mixture of propylene carbonate, ethylene carbonate and dimethyl carbonate in the ratio of 45:40:15.

3. The solid state agent sensor of claim 1 wherein the plurality electrodes comprise a sensing electrode, a reference electrode and a polymer film formed between the plurality of electrodes and the membrane.

4. The solid state agent sensor of claim 1 wherein the electrolyte comprises a solvent mixture of propylene carbonate, ethylene carbonate and dimethyl carbonate in the ratio of 50:40:10.

5. The solid state agent sensor of claim 1 formed within a hand held device for sensing agents of interest.

6. The solid state agent sensor of claim 1 formed to include a fan for turbulent mixing.

7. The solid state agent sensor of claim 1 formed within a disposable button type device for attaching to an outfit.

8. The solid state agent sensor of claim 1 wherein the electrodes are modified to detect bio-warfare agents.

9. The solid state agent sensor of claim 8 wherein the electrodes are sub-micron sized platinum electrodes and are coated electrochemically with a thin layer of platinized-platinum (platinum-black) using a solution of chloroplatinic acid.

10. The solid state agent sensor of claim 9 wherein the resulting platinized electrodes are porous (large surface area) and highly catalytic.

11. The solid state agent sensor of claim 10 where the pores have pore sizes in the range of 50 to 200 Angstroms.

12. The solid state agent sensor of claim 11 wherein the sub-micron sized electrodes are formed to include iridium.

13. The solid state agent sensor of claim 11 wherein the sub-micron sized electrodes are formed to include ruthenium.

14. The solid state agent sensor of claim 11 wherein the sub-micron sized electrodes are formed to include rhodium.

15. The solid state agent sensor of claim 11 wherein the sub-micron sized electrodes are formed to include gold and carbon.

16. The solid state agent sensor of claim 11 wherein the sub-micron sized electrodes are formed to include an alloy.

17. The solid state agent sensor of claim 11 wherein the sub-micron sized electrodes are formed to include an alloy formed of platinum-iridium.

18. The solid state agent sensor of claim 11 wherein the sub-micron sized electrodes are formed to include an alloy formed of platinum-rhodium.

19. The solid state agent sensor of claim 8 wherein the electrodes formed of metal and are coated with a suitable antibody material.

20. The solid state agent sensor of claim 8 wherein the modified electrode surface are formed to be able to bind and immobilize bio-warfare agents forming an antibody-antigen complex.

21. A solid state sensor system, comprising:
at least one integrated circuit, the at least one integrated circuit comprising:
a plurality of test circuits, each of which is biased to test for at least one agent of interest;
each of the plurality of test circuits comprising a plurality of sub-micron inert noble metal electrodes covered by a conduction material; and
each of the plurality of test circuits formed to each generate a signal for biasing the plurality of electrodes for detection of the agents of interest wherein the sensor system is operable to generate a plurality of signals to detect a plurality of agents of interest wherein:
each test circuit comprises a plurality of electrodes and a membrane comprising an electrolyte solution formed within a polymer film to cover the plurality of electrodes for passing the at least one agent of interest to at least a portion of the plurality of electrodes wherein the solid state agent sensor is operable to generate at least one voltage to detect at least one agent of interest, wherein, the electrolyte solution of the membrane covering the plurality of electrodes comprises non-aqueous electrolytes, a stable salt, a polymer matrix materials, fumed silica particles and hydrophobic trimethylsilyl surface groups.

22. The sensor system of claim 21 further comprising a plurality of integrated circuits, each of which contains at least one test circuit for detecting at least one agent of interest.

23. The sensor system of claim 21 formed within a stationary device.

24. The sensor system of claim 21 coupled to communicate with a network.

25. The sensor system of claim 24 wherein the system comprises wireless communication circuitry and is coupled by way of a wireless network.

* * * * *